(12) United States Patent
Zhu et al.

(10) Patent No.: US 10,286,073 B2
(45) Date of Patent: May 14, 2019

(54) MAGNETIC CONTROL OF GENE DELIVERY IN VIVO

(71) Applicants: Haibao Zhu, Houston, TX (US); Sheng Tong, Houston, TX (US); Gang Bao, Houston, TX (US)

(72) Inventors: Haibao Zhu, Houston, TX (US); Sheng Tong, Houston, TX (US); Gang Bao, Houston, TX (US)

(73) Assignee: ILISA TECH, INC., Houston, TX (US)

( * ) Notice: Subject to any disclaimer, the term of this patent is extended or adjusted under 35 U.S.C. 154(b) by 0 days.

(21) Appl. No.: 15/441,089

(22) Filed: Feb. 23, 2017

(65) Prior Publication Data

US 2017/0239370 A1    Aug. 24, 2017

Related U.S. Application Data

(60) Provisional application No. 62/298,875, filed on Feb. 23, 2016.

(51) Int. Cl.
| | |
|---|---|
| *A61K 48/00* | (2006.01) |
| *C12N 15/866* | (2006.01) |
| *C12N 9/22* | (2006.01) |
| *A61K 41/00* | (2006.01) |
| *A61K 9/107* | (2006.01) |
| *C12N 15/113* | (2010.01) |
| *A61K 47/69* | (2017.01) |
| *C12N 15/87* | (2006.01) |
| *A61K 9/50* | (2006.01) |

(52) U.S. Cl.
CPC ............ *A61K 41/00* (2013.01); *A61K 9/1075* (2013.01); *A61K 47/6923* (2017.08); *C12N 9/22* (2013.01); *C12N 15/113* (2013.01); *C12N 15/87* (2013.01); *A61K 9/5094* (2013.01); *C12N 2310/20* (2017.05); *C12N 2320/32* (2013.01); *C12N 2330/51* (2013.01); *C12N 2710/14043* (2013.01)

(58) Field of Classification Search
None
See application file for complete search history.

(56) References Cited

U.S. PATENT DOCUMENTS

| | | | |
|---|---|---|---|
| 2010/0221346 A1* | 9/2010 | Plank | C12N 15/87 424/489 |
| 2014/0179770 A1* | 6/2014 | Zhang | C12N 15/86 514/44 R |

OTHER PUBLICATIONS

Viral Insecticides for Biological Control, editors Karl Maramorosch et al., 1985, Academic Press. Chapter IV, pp. 494-495. (Year: 1985).*
Raty et al., Enhanced Gene Delivery by Avidin-Displaying Baculovirus. Molecular Therapy vol. 9, No. 2, Feb. 2004, p. 282-291. (Year: 2004).*
Kaikkonen et al., How to avoid complement attack in baculovirus-mediated gene delivery. Journal of Invertebrate Pathology 107 (2011) S71-S79 (Year: 2011).*
Yin, H. et al. Genome editing with CAS9 in adult mice corrects a disease mutation and phenotype. Nat Biotechnol 32, 551-553 (2014).
Swiech, L. et al. In vivo interrogation of gene function in the mammalian brain using CRISPR-CAS9. Nat Biotechnol 33, 102-106 (2015).
Dow, L.E. et al. Inducible in vivo genome editing with CRISPR-CAS9. Nat Biotechnol 33, 390-394 (2015).
Nihongaki, Y., Kawano, F., Nakajima, T. & Sato, M. Photoactivatable CRISPR-CAS9 for optogenetic genome editing. Nat Biotechnol 33, 755-760 (2015).
Yin, H. et al. Therapeutic genome editing by combined viral and non-viral delivery of CRISPR system components in vivo. Nat Biotechnol 34, 328-333 (2016).
Stanley, S.A., Sauer, J., Kane, R.S., Dordick, J.S. & Friedman, J.M. Remote regulation of glucose homeostasis in mice using genetically encoded nanoparticles. Nat Med 21, 92-98 (2015).
Wheeler, M.A. et al. Genetically targeted magnetic control of the nervous system. Nat Neurosci 19, 756-761 (2016).

* cited by examiner

*Primary Examiner* — Christopher M Babic
*Assistant Examiner* — Arthur S Leonard
(74) *Attorney, Agent, or Firm* — Boulware & Valoir

(57) ABSTRACT

This disclosure describes a composition and method of magnetic nanoparticles (MNP) that are bound to a baculovirus (BV). The MNP-BV can be systemically administered to a patient, and a strong magnetic field applied to the target tissue, thus allowing uptake and expression only in the target tissue. Off-target effects are not seen because the MNP-BC is inactivated by the complement system outside of the magnetic field.

15 Claims, 9 Drawing Sheets

Specification includes a Sequence Listing.

FIGURE 4a
FIGURE 4b FIGURE 4c
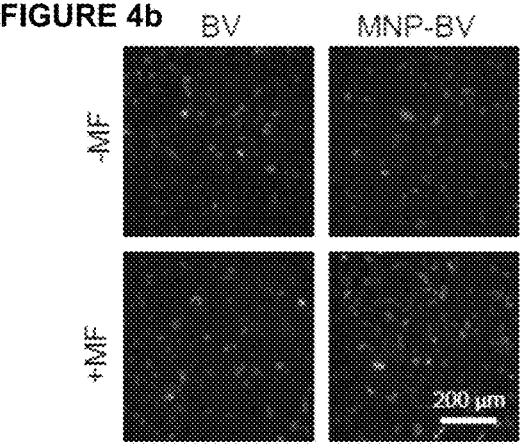
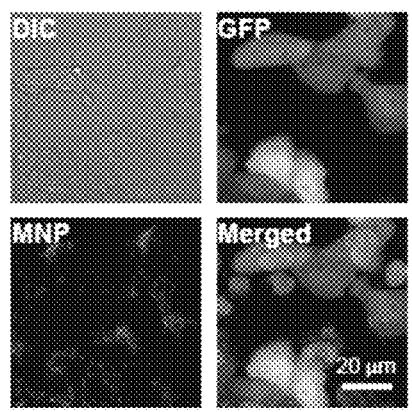
FIGURE 4d
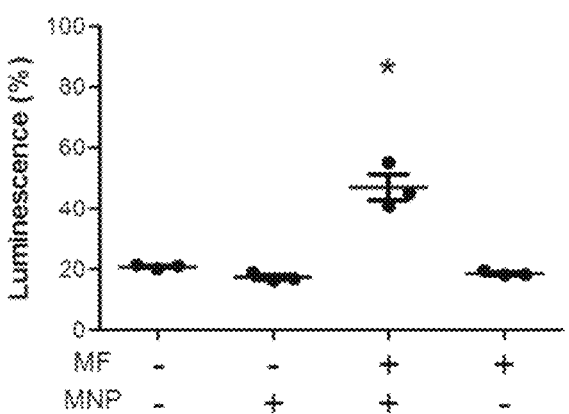

FIGURE 7

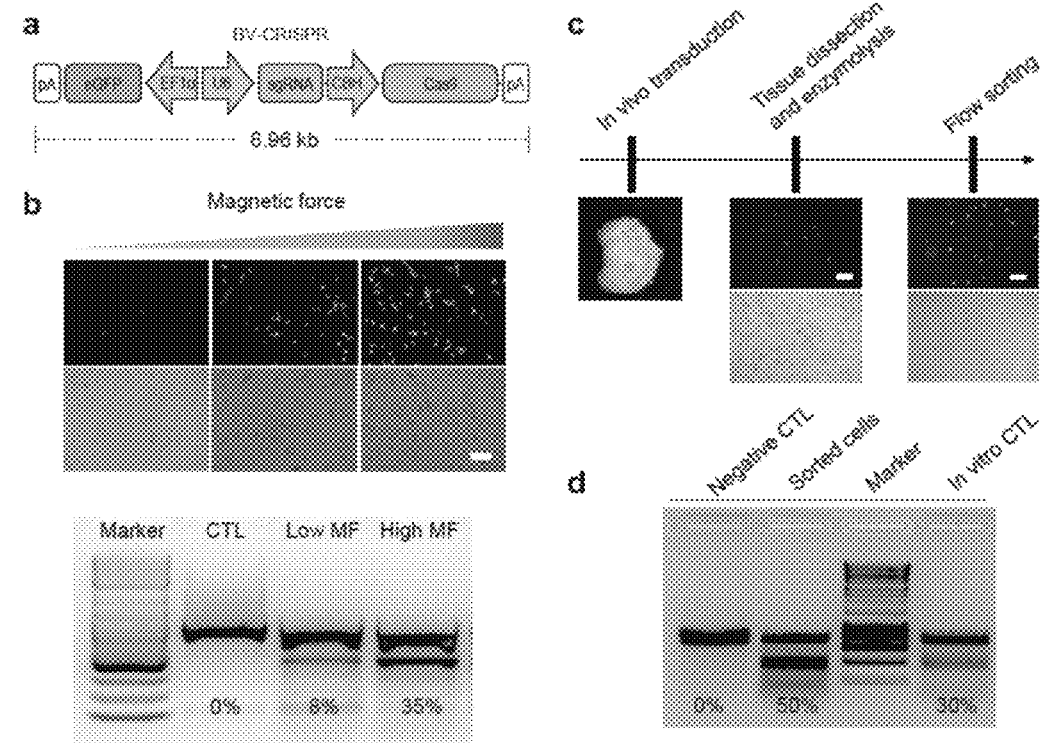

GCTGCTAGCTGTCGCTCTGTGGTTCTGCGTGGAGACCCGAGCC (SEQ ID NO. 5)
GCTGCTAGCTGTCGCTCTGTGG                AGACCCGAGCC (SEQ ID NO. 6)
GCTGCTAGCTGTCGCTCTGTGGT G G G       GACCCGAGCC (SEQ ID NO. 7)
GCTGCTAGCTGTCGCTCTGTG          GCGTGGAGACCCGAGCC (SEQ ID NO. 8)
GCTGCTAGCTGTCGCTCTGTGGTTCT       TGGAGACCCGAGCC (SEQ ID NO. 9)
GCTGCTAGCTGTCGCTCTGTGG     TGCGTGGAGACCCGAGCC (SEQ ID NO. 10)
GCTGCTAGCTGTCGCTCTGTGGTTC    CGTGGAGACCCGAGCC (SEQ ID NO. 11)
GCTGCTAGCTGTCGCTCTGTGGTTC  GCGTGGAGACCCGAGCC (SEQ ID NO. 12)
GCTGCTAGCTGTCGCTCTGTGGTTCATGCGTGGAGACCCGAGCC (SEQ ID NO. 13)
GCTGCTAGCTGTCGCTCTGTGGTTCAATGCGTGGAGACCCGAGCC (SEQ ID NO. 14)

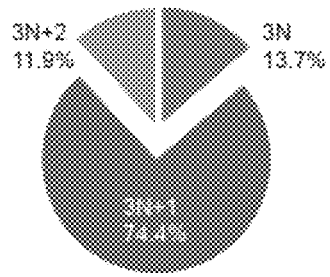

MAGNETIC CONTROL OF GENE DELIVERY IN VIVO

PRIOR RELATED APPLICATIONS

This application claims priority to U.S. Ser. No. 62/298,875, filed Feb. 23, 2016, titled "Magnet Switch For Controlling Gene Delivery In Vivo," and incorporated by reference herein in its entirety for all purposes.

FEDERALLY SPONSORED RESEARCH STATEMENT

This invention was made with government support under PN2EY018244 awarded by NIH. The government has certain rights in the invention.

FIELD OF THE DISCLOSURE

The disclosure generally relates to compositions, methods and systems of in vivo magnetic spatiotemporal control of gene delivery and gene editing using baculovirus, magnetic nanoparticles and a strong magnetic field.

BACKGROUND OF THE DISCLOSURE

The CRISPR system is a revolutionary genome editing technology that can efficiently modify target genes in mammalian cells[1]. It targets a short stretch of DNA via the hybridization of a complementary guide RNA (gRNA) and binding of a CRISPR nuclease, such as CAS9, that recognizes a protospacer adjacent motif (PAM) in the target gene[1]. Preclinical studies have shown that the CRISPR system provides unprecedented opportunities for treating a variety of genetic diseases and infectious diseases[2-6].

Although the CRISPR system can have good targeting efficiency, gRNAs can also hybridize to DNA sequences containing base mismatches. Consequently, the CRISPR system can have off-target activities, causing gene mutations, deletions, inversions or translocations, which may lead to tumorigenic or other deleterious events[7-10]. Therefore, one of the major challenges for in vivo clinical applications of genome editing is to selectively activate the CRISPR system in the desired tissue or organ in order to maximize therapeutic efficacy and reduce genotoxicity.

To improve the specificity of CRISPR systems, many tools have been developed for identifying potential gRNA off-target sites[11], and CAS9 and other CAS nucleases have been designed with controllable nuclease activities[12, 13]. For example, CAS9 proteins have been fragmented into non-functional units, which can dimerize to form active nucleases upon blue light radiation[13]. CAS9 can also be delivered as inducible transgenes that can only be translated in the presence of a chemical cue, e.g. doxycycline[12]. However, for in vivo applications, optical signals cannot penetrate deeply into the body owing to the strong absorption and scattering of light by biological tissues[14], and the chemically-regulated CAS9 expression relies on the biodistribution of transgenes.

An alternative approach to controlling in vivo genome editing is through targeted delivery of the CRISPR system. In particular, the viral vectors with tissue tropism, e.g., the adeno-associated viral vector (AAV)[15], are being explored for tissue-specific genome editing in vivo[3, 10, 16]. However, most viral vectors for in vivo gene delivery are derived from viruses originating from human or other mammals. It is difficult to control the systemic dissemination and replication of these viral vectors used for in vivo genome editing, which increases the risk of genotoxicity[4, 17]. Furthermore, vectors derived from small viruses, such as AAV and LV, have packaging limits, thus limiting the size of the genetic material that can be introduced. In addition, many viruses are targeted by the complement cascade for inactivation, thus limiting their efficiency.

The Baculoviridae is a family of viruses that infect insects and are very large—their circular double-stranded genome ranging from 80-180 kbp. Because of this large size, they have great potential as a vector, and many such vectors are in use since Dr. Max Summers developed the first baculovirus expression vector system.

The large size of BVs allows an extraordinary DNA packing capacity compared to most other viruses, thus enabling the integration of multiple gene expression cassettes into a single viral vector[23]. Although the baculovirus and their vectors lack the ability to replicate in mammalian cells, they can transduce mammalian cells with high efficiency and low cytotoxicity, providing a robust and transient gene expression[22-25]. However, there have been very limited in vivo applications of BVs because of their inactivation by the complement cascade in the serum[24, 26].

The complement system represents a first-line host defense of the innate immune system designed to eliminate foreign elements, such as insect viruses. It has been well established that BV administrated intravenously can circulate throughout the body, and the complementary factor C3 in the blood will bind to circulating BV and initiate molecular events that eventually lead to BV inactivation (FIG. 1)[26]. Indeed, triggering of the complement cascade is a major cause for the inactivation of a variety of currently used gene delivery vectors and contributes to inefficient gene transfer rates after in vivo application.

Thus, what is needed in the art are better nucleic acid delivery methods, products, and systems that solve or at least mitigate one or more of the above limitations. The ideal gene delivery mechanism would allow targeted delivery of nucleic acid, and avoid off-target effects.

SUMMARY OF THE DISCLOSURE

This disclosure shows that by complexing magnetic nanoparticles (MNP) with recombinant baculovirus (BV) to form a delivery vehicle (MNP-BV), CRISPR mediated genome editing can be activated locally and transiently in vivo with an external magnetic field. Since BV delivered through intravenous injection will normally be inactivated due to innate immune response, it has not been used widely for in vivo gene delivery. We show herein that a locally applied magnetic field early in the process enhances the margination and endocytosis of circulating MNP-BV, thereby avoiding BV inactivation. The BV then triggers a transient transgene expression of the encoded CRISPR system in the target tissue, enabling tissue-specific in vivo genome editing.

In the studies described herein, we prove that the serum inactivation can be utilized as an "off" switch to limit systemic or non-target activities of BV, and an external magnetic field can serve as an "on" switch for tissue-specific genome editing owing to the margination and internalization of the MNP-BV complex. This hybrid nanoparticle-viral vector system provides a unique delivery vehicle for CRISPR-mediated in vivo genome editing with precise spatiotemporal control.

The magnetic nanoparticles overcome the serum-associated inactivation of baculovirus and allow for targeting a specific organ or tissue type by using an applied magnetic field. This is not just a concentration dependent effect, because using 10× as much BV does not improve efficiencies. Instead, the application of a magnetic field vastly improves the kinetics of uptake, possibly via increased margination of BV and cellular responses to the magnetic force exerted on the cell membrane, allowing the cells to take in the BV and their payload before the complement system can inactivate the virus.

This technology has the ability to package plasmids or other vectors encoding CAS9 or other CAS proteins, single or multiple guide RNAs and the DNA donor template all into a single viral vector, and target a specific organ or tissue in vivo by targeted application of a magnetic field shortly after viral delivery, thus becoming a powerful tool for in vivo genome editing. The invention can also be used ex vivo, and transformed cells or tissue reintroduced back into a living system, but its real value lies in in vivo uses, where the complement system would otherwise inhibit BV transduction, and can be used to suppress off-target effects.

The major steps involved are: (1) package the plasmids encoding a CAS protein such as CAS9, one or more guide RNA(s) and donor template into baculovirus; (2) attach magnetic nanoparticles to baculovirus; (3) introduce the MNP-BVs to an animal or patient, and (4) apply an magnetic field to activate the MNP-BV complex in a specific organ or tissue.

As used herein a "CRISPR system" or "CRISPR gene editing system" includes the clustered regularly interspaced short palindromic repeats (pronounced crisper) that provides prokaryotic immune systems that confers resistance to foreign genetic elements. Generally, the system as modified for gene editing uses a CAS9-like protein, one or more guide RNA(s) and an optional donor template. However, other CAS proteins are known and could be used.

As used herein, the term "CAS9" or "CRISPR associated protein 9" is a nuclease that functions in a CRISPR system. It is the most commonly used "CRISPR nuclease." The term CAS9 includes any member of the CAS9 family of genes/proteins or synthetic variants or fusion proteins thereof that function in a CRISPR system, as well as deactivated CAS9 (dCAS9). Examples include *Streptococcus pyogenes* CAS9 (SpCAS9) and *Staphylococcus aureus* (SaCAS9). The term "CAS9" also includes modified CAS9 or dCAS9 proteins with amino acid sequence deletion, insertion and/or mutation.

Other CRISPR nucleases could be used as well, e.g., nuclease Cpf1 discovered in the CRISPR/Cpf1 system of the bacterium *Francisella novicida*, and CjCAS9 from *Campylobacter jejuni*. Other CRISPR nucleases include Cas8a, Cas5, Cas8b, Cas8c, Cas10d, Cse1, Cse2, Csy1, Csy2, Csy3, GSU0054, Cas10, Csm2, Cmr5, Cas10 or Csx11, Csx10, Csf1, Csn2, Cas4, Cpf1, C2cI, C2c3, and C2c2 and more are being discovered all the time.

As used herein the term "guide RNA" or "gRNA" includes crRNA, tracrRNA and their combination (sgRNA). A crRNA sequence contains the target RNA sequence to locate the correct section of DNA, which binds to e.g., a CAS9 nuclease-recruiting sequence "trans-activating crRNA" (tracrRNA) to form a single guide RNA (sgRNA). The term "guide RNA" or "gRNA" also includes crRNA, tracrRNA and sgRNA with chemical modifications, with additional RNA sequences for tagging and binding to other proteins.

The "guide RNA" or "gRNA" acts as a guide for the endonuclease CAS9 and should be suitable for use with the selected CAS9 or dCAS9 or other nuclease proteins.

It is known in the art how to design such gRNA sequences for the target gene of interest. Generally speaking, the 3' end of the DNA target sequence must have a protospacer adjacent motif (PAM) sequence (e.g., 5'-NGG-3' for SpCAS9). With SpCAS9, the 20 nucleotides upstream of the PAM sequence is the targeting sequence and CAS9 nuclease will cleave the DNA target sequence 3 bases upstream of the PAM. The best CAS9-based sgRNAs for several tested genes have a G at position 1 and an A or T at position 17. The target sequence can be on either DNA strand of the target gene.

Note that while, the PAM sequence itself is absolutely required for cleavage, it is NOT part of the sgRNA target sequence. There are several online tools (e.g., CRISPR Design or CHOPCHOP) that detect PAM sequences and list possible crRNA sequences within a specific DNA region. These algorithms also predict off-target effects elsewhere in the genome, allowing one to choose the most specific crRNA for the application.

As used herein, the "donor template" provides a copy of the gene or a part of the gene that is intended to replace the endogenous sequence (usually used to correct a defective gene), or to insert a DNA sequence. It is optional, however, and the same system without a donor template will typically modify a gene through small insertions and deletions (indels) as a result of non-homologous end joining (NHEJ) of the DNA double strand break (DSB) caused by the CRISPR system, or knock out a gene or genes through large deletions by two CRISPR/CAS9 induced DSBs.

As used herein, "BV" usually means baculovirus vector, unless it is apparent that we are discussing the wild type virus from the context. The two are similar, but it is understood that the virus usually has been modified to make the vector by replacing the naturally occurring polyhedrin gene in the wild-type baculovirus genome with a recombinant gene or cDNA. Other modifications can also be included for efficiency, such as the inclusion of a multicloning site, selectable markers, a plasmid origin of replication, and the like.

As used herein, "gene editing" includes both functional changes to a protein's activity as well as changes in gene regulation. Thus, the changes need not lie within the open reading frame but can significantly far up or downstream.

As used herein, a "MNP" means a magnetically responsive particle of <200 nm average size, preferably <100 nm.

One preferred MNP comprises a magnetic powder or crystal, such as magnetite ($Fe_3O_4$), coated with a biocompatible and hydrophilic molecules. The coating molecules can chemically bind to the iron oxide surface via reactive groups such as amine, hydroxyl or carboxyl groups or physically absorbed onto the iron oxide surface via hydrophobic interactions, e.g. coating with a co-polymer of phospholipid and poly(ethylene glycol) that forms a micellar layer around the crystal. The coating molecules should be immunocompatible and/or nontoxic. Other targeting peptides, such as receptors or antibodies or cell penetrating peptides, such as TAT, can be conjugated to to MNP-BV complexes.

As used herein "magnetically responsive element" can be any element or molecule that will create or respond to a magnetic field. The magnetically responsive element can be iron (I) oxide, iron (II) oxide, iron (III) oxide aka magnetite, $Fe_{16}N_2$, Iron-nickel, hematite, maghemite, iron oxide nanocrystals doped with other elements such as zinc, manganese, cobalt, and magnetic nanocrystals formed by other magnetic elements such as manganese, cobalt. These magnetically responsive elements are used in powdered or crystal form, with average diameter <100 nm, preferably <50 nm, or about 10-20 nm. The layer of the coating molecules on the magnetically responsive elements should be less than 20 nm in thickness and the entire coated particle is preferably less than 40 nm in diameter.

"Magnet" refers to any material creating a magnetic field and can be a permanent magnet or an electromagnet. Preferably, a rare earth magnet is employed. Examples of rare earth magnets suitable for use with the present invention include, but are not limited to, neodymium rare earth magnets, samarium-cobalt rare earth magnets, $Nd_2Fe_{14}B$, $SmCo_5$, $Sm(Co,Fe,Cu,Zr)_7$, $YCO_5$, or any combination thereof.

Neodymium rare earth magnets are the strongest and most affordable type of permanent magnet, and are generally preferred, but samarium-cobalt magnets have a higher Curie temperature (the temperature at which the material loses its magnetism) and may be preferred for uses involving high sterilization temperatures.

Particular types of rare earth magnets may also be selected as desired according to the conditions to which the rare earth magnets may be exposed. For example, any of the following factors may be considered in selecting a type of rare earth magnet: remanence (Br) (which measures the strength of the magnetic field), coercivity (Hci) (the material's resistance to becoming demagnetized), energy product (BHmax) (the density of magnetic energy), and the Curie temperature (Tc). Generally, rare earth magnets have higher remanence, much higher coercivity and energy product than other types of magnets. Where high magnetic anisotropy is desired, $YCO_5$ may be suitable for use.

In place of or in addition to the rare earth magnets, powered magnets may be used in the methods of the invention, and batteries or grid power may be used to power the magnets as desired. Alternatively, RF or other electromagnetic radiation activated power sources can be used to power the magnet, such as is used with RFID tags. Such an embodiment may be particularly useful where a narrow, needle-like probe is inserted into the tissue of interest to create a strong local magnetic field.

We can elaborate a number of principals for the selection of magnetic size, strength and shape. Firstly, the magnet size and shape are confined by the size of the body tissue with which it will be used, as excess magnet is both a waste of resources and expands the treatment area beyond the target tissue. Second, the distance of the magnet from the tissue can vary with increasing field strength, stronger magnets capable of being held farther away than weak magnets. These considerations must be balanced against the stength of the magnet (how far away the magnet can be and still attract MNP).

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations may be used herein:

| ABBRE-VIATION | TERM |
|---|---|
| ALT | Alanine transaminase |
| AMS | Adult mouse serum |
| AST | aspartate aminotransferase |
| AVV | Adeno-associated virus |
| BV | Baculovirus or baculovirus vector |
| Cas | CRISPR-associated genes, e.g., CAS9 |
| crRNA | CRISPR RNA |
| Csn1 | a CRISPR-associated protein containing two nuclease domains, that is programmed by small RNAs to cleave DNA |
| dCAS9 | deactivated CAS9 |
| DSB | Double-Stranded Break |
| DSPE | 1,2-Distearoyl-sn-glycero-3-phosphoethanolamine |
| $Fe(acac)_3$ | Iron(III) acetylacetonate |
| gRNA | guide RNA |
| HDR | Homology-Directed Repair |
| HNH | an endonuclease domain named for characteristic histidine and asparagine residues |
| HUVEC | Human umbilical vein endothelial cells |
| Indel | insertion and/or deletion |
| LV | Lentivirus |
| MF | Magnetic field |
| MTT | 3-(4,5-dimethylthiazol-2-yl)-2,5-diphenyltetrazolium bromide |
| MOI | Multiplicity of infection |
| MPEG | methoxypoly(ethylene glycol) |
| NHEJ | Non-Homologous End Joining |
| PAM | Protospacer-Adjacent Motif |
| PEG | poly(ethylene glycol) |
| PFU | Plaque forming unit |
| ROI | Region of interest |
| RuvC | an endonuclease domain named for an *E. coli* protein involved in DNA repair |
| SEM | standard error of the mean |
| sgRNA | single guide RNA |
| TALEN | Transcription-Activator Like Effector Nuclease |
| TEM | Transmission electron microscopy |
| tracrRNA, trRNA | trans-activating crRNA |
| WT | Wild type |
| ZFN | Zinc-Finger Nuclease |

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4(a)-(d). Nanomagnets improve BV-mediated transgene expression in vitro. (a) Expression vectors carrying the plasmids for luciferase (BV-LUC) and eGFP (BV-eGFP) respectively were used for this proof of concept experiment. Hepa 1-6 cells (a mouse liver tumor line, ATCC CRL-1830) were incubated with BV or MNP-BV for 30 minutes with or without a magnetic field directing the MNP-BV complexes to the cell surface. (b) Fluorescence images of BV-mediated eGFP expression. (c) Co-localization of eGFP (green) and MNPs (red) in the cells treated with MNP-BV-eGFP. (d) BV-mediated luciferase expression. The luciferase activity was normalized with that from the cells incubated with BV alone for 4 hours. The transgene expression of BV was enhanced by the combination treatment with MNPs and a magnetic field, while the effect of MNPs or the magnetic field alone was negligible. Data represent mean±standard error of the mean (SEM); n=3 per group.

FIG. 7(a)-(e). Magnetic field enables spatial control of genome editing. (a) BV-CRISPR expression vectors. eGFP expression cassette, guide RNA and CAS9 expression cassette can all be integrated into one vector. eGFP was used for identifying transduced cells. (b) Magnetic field-triggered mouse VEGFR2 gene editing in vitro. The cells were incubated with MNP-BV (MOI 100) in culture medium containing 50% of AMS for 30 minutes in the presence of a magnetic field generated with a NdFeB block magnet. Transgene expression was examined by eGFP fluorescence at 24 hours after transduction. There was no transgene expression in the cells without the magnetic treatment. The level of transgene expression increased with the strength of the magnetic field, which was controlled by the distance between the cells and the magnet. After 48 hours, the cells were harvested and examined with the T7E1 assay, which detects heteroduplex DNA that results from annealing DNA stands that have been modified after a sgRNA/CAS9 mediated cut to DNA strands without modifications. We use this assay to obtain a first estimate of whether our targeting was successful or not. Consistent with the trend in eGFP expression, the CRISPR-mediated VEGFR2 disruption correlated with the magnetic field strength. (c) Flow chart of cell purification of CRISPR/CAS9 targeted cells from the mouse liver. (d) Analysis of in vivo mouse VEGFR2 gene editing using T7E1 assay. (e) Representative mutation patterns detected by deep sequencing of mouse VEGFR2 locus. Top, wild-type sequence and PAM sequence marked in magenta; blot, deleted bases; blue bases, insertions or mutations (indels).

FIG. 8A. The transduction efficiency increases with the magnetic field strength. The magnetic field strength was controlled by changing the distance between Hepa 1-6 cells and the magnet. The distance between the cells and the N52 grade NdFeB magnet was 0.05 mm and 0.5 mm in high MF and low MF conditions, respectively. FIG. 8B. The transduction efficiency increases with the length of magnet treatment, efficiency increasing significantly at 1 hr. C. The transduction efficiency increases with the ratio between MNP and BV. The viruses ($10^6$ PFU) were mixed with designated amount of MNPs for 20 minutes. The cells were incubated with the mixture for 30 minutes in a magnetic field. The transduction dosage was 100 PFU per cell. Data represent mean±SEM; n=4 per group.

DETAILED DESCRIPTION

Figure 1:
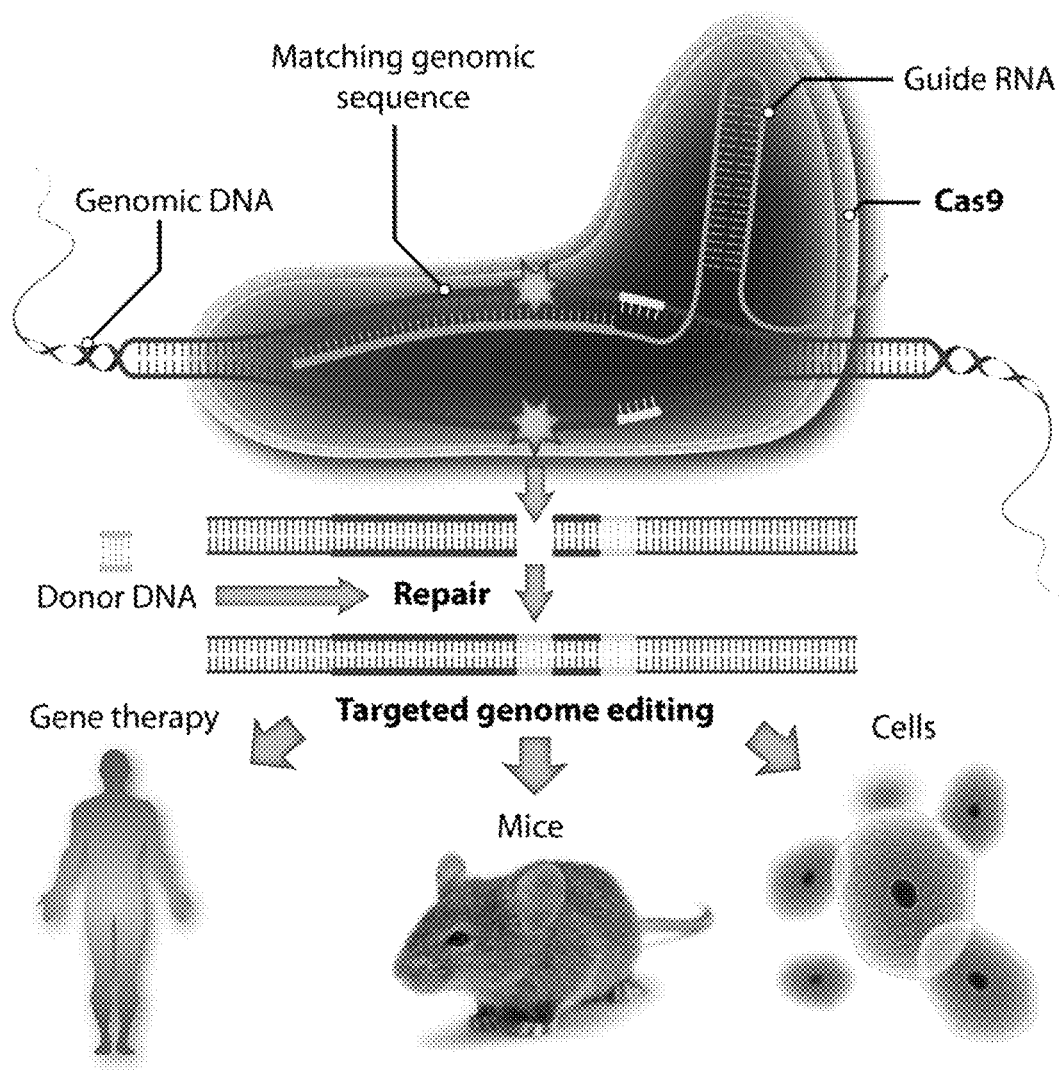
FIG. 1. Genome Editing using CRISPR/CAS9. The simplicity of the CRISPR nuclease system, with only three components (CAS9, crRNA and trRNA) makes this system amenable to adaptation for genome editing. By combining the crRNA and trRNA into a single synthetic guide RNA (sgRNA), a further simplified two component system can be used to introduce a targeted double stranded break. This break activates repair through error prone non-homologous end joining (NHEJ) or Homology directed Repair (HDR). In the presence of a donor template with homology to the targeted locus, the HDR pathway operates allowing for precise changes to be made to the target gene. In the absence of a template, NHEJ is activated resulting in insertions and/or deletions (indels) which disrupt the target locus.

We have combined two important tools (CRISPR and BV) to develop a novel way of genome editing. In order to overcome serum inactivation of the insect virus, we combine the virus with magnetic nanoparticles, inject or otherwise introduce the virus in vivo, and then subject the target tissue to a strong magnetic field within 30 minutes, preferably within 10", of viral introduction. This allows the virus to escape complement inactivation and allows transient expression of the CRISPR payload. Meanwhile, tissues that are not suject to the magnetic field will not take up virus, because any virus outside the target zone will be inactivated.

We have exemplified the method using a CAS9/CRISPR genomic editing tool, but the method is of broader application and can be used to deliver other genome editing tools or other agents, such as drugs or other DNAs or RNAs and the like.

In more detail, the invention includes any one or more of the following in any combination(s) thereof:

---

A method of targeted in vivo gene editing, said method comprising:
a) packaging an expression vector (V) encoding a gene editing system;
b) attaching a plurality of magnetic nanoparticles to said V to make MNP-V;
c) introducing said MNP-V to a patient having a gene to be edited;
d) applying a magnetic field to a targeted tissue, without applying said magnetic field to nontargeted tissue, so that the MNP-V are only taken up and expressed in cells in said targeted tissue; and
e) thereby editing said gene in said targeted tissue in said patient.

A method of targeted in vivo gene editing, said method comprising:
a) packaging an expression vector encoding a CAS9 or dCAS9 protein, single or multiple guide RNAs and an optional donor template into a baculovirus vector (BV), wherein said guide RNA and said optional donor template have homology to one or more gene(s) that is to be edited;
b) attaching a plurality of magnetic nanoparticles to said BV to make MNP-BV;
c) introducing said MNP-BV to a patient comprising said gene(s) to be edited;
d) applying a magnetic field to a targeted tissue, without applying said magnetic field to nontargeted tissue, so that the MNP-BV are only taken up and expressed in cells in said targeted tissue; and
e) thereby editing said gene(s) in said targeted tissue in said patient.

A method of targeted in vivo gene editing, said method comprising:
a) packaging an expression vector encoding a CRISPR nuclease, single or multiple guide RNAs and an optional donor template into a baculovirus vector (BV), wherein said guide RNA and said donor template have homology to one or more gene(s) that is to be edited in a targeted tissue;
b) attaching a plurality of magnetic nanoparticles to said BV to make MNP-BV wherein a ratio of MNP to BV is at least 500:1;
c) introducing said MNP-BV to a patient having said gene to be edited;
d) applying a magnetic field of at least 0.1 Tesla and 0.1 Tesla/m to said targeted tissue within 10 minutes of said introducing step c, without applying said magnetic field to nontargeted tissue, so that the MNP-BV are only taken up and transiently expressed in cells in said targeted tissue; and
e) thereby editing said gene in said targeted tissue in said patient.

Any method herein described, wherein said magnetic field is at least 0.1 Tesla.
Any method herein described, wherein said gradient of the magnetic field is at least 0.1 Tesla/m.
Any method herein described, wherein said magnetic field is applied within 5", 10", or 30" of said introducing step c.
Any method herein described, wherein said magnetic field is applied for at least 30 minutes, or at least an hour or more.
Any method herein described, wherein said MNP:BV ratio is at least 500:1.
Any method herein described, wherein said guide RNA is a synthetic guide RNA comprising a gRNA and a trRNA.
Any method herein described, wherein said magnetic field is at least 0.1 Tesla and the gradient of the magnetic field is at least 0.1 Tesla/m.
Any method herein described, wherein said expression vector is a baculovirus vector and said gene editing system comprises a CRISPR system.
Any method herein described, wherein said MNP are made with iron oxide nanoparticles.
Any method herein described, wherein said MNP are made with iron(III) oxide nanoparticles and said nanoparticles are coated with one or more biocompatible polymers.

Any method herein described, wherein said MNP are made with magnetite crystals of 10-50 nm and said crystals inside a biocompatible phospholipid micelle.

Any method herein describes, which is performed on ex vivo tissue rather than a whole animal.

An MNP-BV made by the methods herein described.

A transformed cell or tissue or animal made by the methods herein described.

Methods

Production of BV Vector:

BV constructs including BV-LUC, BV-eGFP and BV-CRISPR, were generated using pFB-CMV-LUC, pFB-EF1a-eGFP and pFB-EF1a-eGFP-U6-sgRNA-CBh-CAS9, respectively, and propagated in Sf9 insect cells using the Bac-to-Bac Baculovirus Expression System (Thermo Fisher) according to the distributor's protocol.

Synthesis of MNPs:

Magnetic iron oxide nanoparticles (MNPs) were synthesized according to previously published protocols[29, 30]. In brief, magnetic nanocrystals were synthesized through thermodecomposition of iron(III) acetylacetonate ($Fe(acac)_3$, Sigma) in benzyl ether using oleic acid (Sigma) and oleylamine (Sigma) as the capping molecules.

As-synthesized nanocrystals were subsequently coated with DSPE-mPEG2000 (Avanti lipids) and DSPE-PEG-maleimide (Avanti lipids) at a molar ratio of 9:1 using a dual solvent exchange method.

To conjugate TAT peptides to the surface of MNPs, freshly coated MNPs were mixed with cys-TAT peptides (CGYGRKKRRQRRR, Genscript) at a molar ratio of 1:400 in PBS and incubated overnight. Unconjugated TAT peptides were removed by washing the nanoparticles with deionized water in centrifugal filter tubes (cutoff mol. wt.=100 kDa). The physical properties of the MNPs were characterized using transmitted electron microscopy (TEM), dynamic light scattering (DLS) (Mobius, Wyatt) and SQUID (MPMS, Quantum Design).

In Vitro BV Transduction:

Hepa 1-6 mouse liver cell line was purchased from ATCC (CLR-1830). Human umbilical vein endothelial cells (HUVEC) were purchased from Lonza (CC-2517). These cell lines were tested for mycoplasma contamination but not authenticated after receiving them. All cells were cultured according to the standard protocols from the distributors.

In a typical in vitro BV transduction experiment, the cells were seeded in a chamber slide. Before BV transduction, 2 μL of BV suspension was mixed with 4 μL of MNPs for 20 minutes. The cells were then incubated with the mixture for 30 minutes with or without the magnet. In each group, the cells were transduced with BV at an MOI of 100 PFU per cell unless otherwise specified. After transduction, the cells were incubated with fresh medium. After 24 hours post transduction, luciferase activity was measured using an in vitro luciferase kit in a microplate reader (ONE-Glo™ Luciferase Assay System, Promega). EGFP fluorescence was examined using flowcytometry or fluorescence microscopy.

In Vitro gDNA Analysis:

Hepa 1-6 cells were seeded in chamber slides and transduced with BV or MNP-BV as discussed above. Genomic DNA was extracted from treated cells with a DNeasy Blood and Tissue Kit (Qiagen). The amplicon containing the CRISPR cutting site was amplified with the indicated primers (F: CCCCCATTCGCTAGTGTGTA (SEQ ID NO:1); R: AGCACGGAGTGATTGATGCC (SEQ ID NO:2)) using Platinum® PCR SuperMix High Fidelity kit (Invitrogen). The PCR products were purified with a PCR purification kit (Qiagen) and denatured, reannealed and digested with a T7E1 nuclease (New England BioLabs). The fragments were examined by gel electrophoresis in 1.5% agarose gel.

Cytotoxicity Study:

Hepa 1-6 cells were cultured in 96-well plates and incubated with BV at designated MOIs with or without MNPs for 12 hours. After treatment, the cells were incubated in fresh medium for 3 days and cell viability was evaluated by MTT assay. In brief, MTT was dissolved in sterile PBS at 5 mg/mL and added to the culture medium at 20 μL per well. After 4 hour incubation, the supernatant was removed and DMSO was added to the cells at 150 μL per well to dissolve the formazan generated by the cells. The optical density of the solutions was measured at 490 nm using a microplate reader.

Immunostaining:

The cells were seeded in chamber slides and incubated with BV or MNP-BV under designated conditions. After treatment, the cells were fixed in 4% paraformaldehyde for 20 minutes, permeabilized with PBS containing 0.1% Triton for 3 minutes and blocked with 5% BSA for 1 hour at room temperature. BV was detected by incubating the cells with an antibody against VP39 (the late capsid protein of BV, kindly provided by Prof. Loy Volkman and Dr. Taro Ohkawa) overnight at 4° C. followed by an Alexa Fluor 647 goat anti-mouse IgG antibody (Abcam)[35]. After that, the cells were stained with Hoechst 33342 (Thermo Fisher) and Alexa Fluor 488 phalloidin (Thermo Fisher). The images were acquired with a confocal microscope (Zeiss LSM 710).

In Vivo BV Transduction:

All animal studies were approved. Athymic nude mice ~25 g body weight were purchased from Charles River. C3 knockout mice were purchased from the Jackson Laboratory. The mice were randomly allocated to the experimental groups (n=3 per group) without blinding. The mice were injected with BV ($10^9$ PFU) with or without MNPs (0.1 mg Fe) dispersed in 200 μL sterile PBS through the tail vein.

Figure 6A:
FIG. 6(a)-(h). Magnetic field enables tissue-specific transgene expression in vivo. (a) BV-LUC expression vector. (b) Schematic diagram of in vivo MNP-BV-based transgene delivery. The hybrid vehicle with luciferase expressing cassette was administrated to the mouse through intravenous injection. A block magnet was pressed by pressing against the belly to trigger local transgene expression in the mouse liver. The contour plot indicated the magnetic force applied to individual MNPs at a distance of 1 mm from the top of the magnet. (c) and (d) Bioluminescence analysis of transgene expression. Nude mice were injected with PBS, BV alone, MNP-BV, and MNP-BV followed with magnetic field (MF) treatment for 60 minutes. In the positive control, C3 knockout mice were injected with BV alone. In all groups, the dosage of the virus was $10^9$ PFU per mouse. After 24 hours post-injection, the mice were imaged using an IVIS™ small animal live imaging system. Panel (d) plots the bioluminescence value in a region of interest (ROI) enclose the liver. Note that the magnetic field (MF) triggered high transgene expression in mice injected with MNP-BV, while without the magnetic treatment, the signal was negligible due to serum inactivation. Panels (e) and (f) show in vivo biodistribution of transgene expression. In MNP-BV+MF group, the organs were isolated 24 hours after injection, and bioluminescence of vital organs was measured ex vivo. As shown in the inset, the liver showed a high level of transgene expression, while bioluminescence was undetectable in the lung, kidney, spleen, and heart. All luminescence activity was normalized to the peak value in the plot. Panels (g) and (h) show in vivo transgene expression at 24 hours and 48 hours post-injection. Data represent mean±SEM; n=3 per group.
Figure 6B:
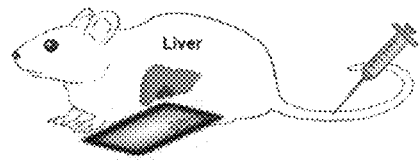
Figure 9A:
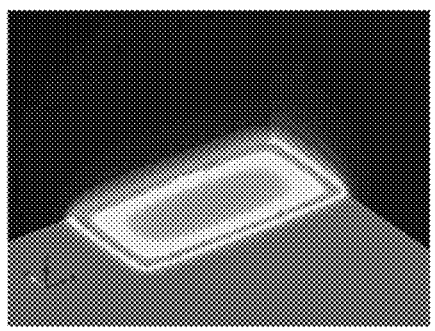
FIG. 9A-B. Numerical simulation of the magnetic force field generated by a NdFeB block magnet. A magnet will produce a magnetic field that varies according to shape and distance from the magnet. Therefore, a magnet is typically easily characterized by a single value, and we have therefore produced a numerical simulation of the field for the magnet employed. The dimension of the magnet is L×W×H=1"×½"×½" and the remanent magnetization is 1.48 Tesla along the z-axis. The magnetic field and the magnetic force exerted on individual MNPs were simulated with COMSOL Multiphysics. A. The distribution of the magnetic force along z-direction on xy-, yz- and zx-planes at the corner of the block magnetic. B. The distribution of magnetic force along z-direction on the zx-plane in (A).
Figure 9B:
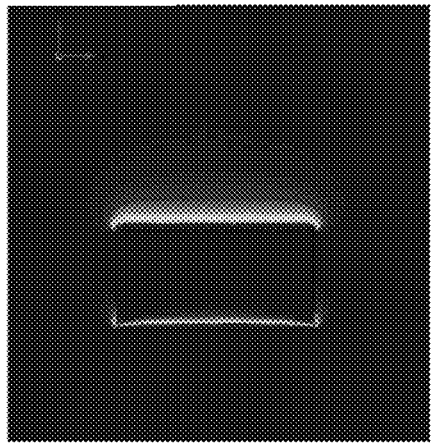

Injected mice were placed on an N52 grade NdFeB block magnet (L×W×H=1"×½"×½") (K&J Magnetics) for one hour under anesthesia (FIG. 6b). The magnetic field and the magnetic force exerted on individual MNPs were simulated with COMSOL Multiphysics (FIG. 9). To examine the luciferase activity resulting from BV transduction, each mouse was injected with in vivo luciferase substrate (Promega) intraperitoneally (i.p.) and imaged using an IVIS Kinetic III live imaging system (Perkin Elmer).

To examine the outcomes of genome editing, organs were harvested at 1 or 4 days after injection of baculovirus. Individual liver cells were isolated from the liver tissue using Liver Dissociation Kit (Miltenyi Biotec). Genome editing was evaluated with next generation sequencing using the following primers: F—TGAAAGAACAC-CCAAGGGAGG (SEQ ID NO:3) and R—GGGACGGA-GAAGGAGTCTGT (SEQ ID NO:4).

To examine the in vivo toxicity of MNP-BV, vital organs and blood were harvested from treated mice after 10 days post injection. The organs were fixed in 10% formalin solution overnight and embedded in paraffin. Histology evaluation was performed in tissue sections stained with hematoxylin and eosin. Alanine transaminase (ALT) and aspartate aminotransferase (AST) levels in the blood were measured using the ALT ELISA Kit (Biocompare) and AST Colorimetric Kit (Biovision) respectively, according to the manufacturer's instructions.

Statistics:

SPSS Statistics (SPSS) was used for all calculations. Data was analyzed using Student's t-tests or one-way ANOVA and post hoc multiple comparison tests. The difference with $p<0.05$ was considered statistically significant (* denotes $p<0.05$; # denotes $p<0.01$).

Results and Discussion

Recombinant BV was produced as described above. Magnetic iron oxide nanoparticles (MNPs) that can bind to BV were synthesized in three steps. First, magnetite nanocrystals were synthesized through thermodecomposition of iron acetylacetonate in benzyl ether[29]. As-synthesized nanocrystals were 15.5±1.1 nm in diameter and had a saturation magnetization of 87.2 emu/g, similar to that of bulk magnetite.

Figure 3A:
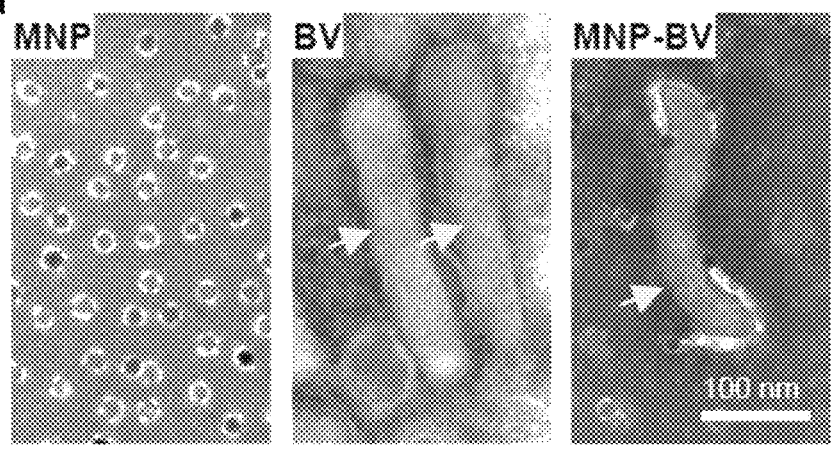
FIG. 3(a)-(b). Nanomagnets improve endocytosis of BV. (a) Representative TEM images of MNPs, BVs, and MNP-BV hybrids via TAT. The samples were negatively stained with phosphotungstic acid. In the left panel, the white corona surrounding the dark cores is the phospholipid coating layer of MNPs. The right panel shows multiple MNPs (red arrows) may be associated with a single BV through TAT. (b) MNPs under the external magnetic field enhanced endocytosis of BV. Cells incubated with BV alone (left panel) or MNP-BV (right panel) under a magnetic field were stained and examined with fluorescence microscopy. Blue, nucleus; Green, actin fibers; Red, BV stained with an anti-VP39 antibody to detect the BV capsid protein. In the presence of an external magnetic field, BV complexed with MNPs are rapidly internalized by cells compared to BV alone.

Water-dispersible MNPs were then generated by coating the nanocrystals with copolymers of phospholipid and poly (ethylene glycol) using a dual solvent exchange method[25] to form micelles around the crystals. MNPs were then conjugated with the TAT peptide, a positively charged peptide that can attach to the BV surface (FIG. 3a)[30, 31]. However, this step is optional as the MNPs were sufficient to protect and deliver the BV to the cells without the TAT. TAT peptide conjugation to MNP was confirmed by zeta potential measurements and DNA retardation assay. When TAT-conjugated MNPs were mixed with BVs in phosphate buffered saline (PBS), multiple MNPs could attach to a single BV to form the BV-MNP hybrid, presumably due to electrostatic interactions (FIG. 3a).

MNPs can disperse in aqueous buffers with negligible magnetic interactions, but upon exposure to a magnetic field, they migrate against the field gradient as nanomagnets. In this study, the magnetic field was generated by using NdFeB magnets with a residual induction of 1.48 Tesla (see FIG. 9). When a mixture of BV and MNP were infused through a silicone tubing at physiologically relevant flow rates, more than 50% of BV could be captured by a block magnet placed next to the tubing, as determined by a viral titration assay. This suggests that hybrids of BV and MNP were formed and that the block magnet was effective in attracting the BV-MNP complex to a specific location.

Figure 3B:
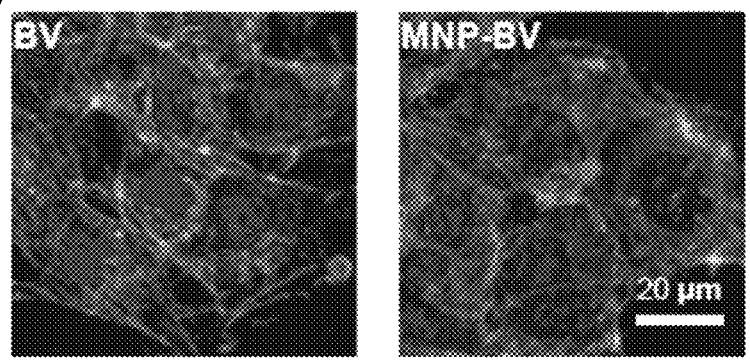

We next investigated the effect of nanomagnets on the interactions of BV with cultured Hepa 1-6 cells, which are known to have high BV infectibility[32]. BV alone exhibited negligible attachment to the cell surface as examined by immunostaining with the anti-vp39 antibody, which detects a BV capsid protein (FIG. 3b)[33, 32]. In contrast, with the applied magnetic field, a large amount of MNP-BV complexes became attached to the cell surface and entered the cytoplasm after 10 min incubation (FIG. 3b). TEM images of cell cross-sections show co-existence of MNP and BV in the lysosomes, indicating cellular internalization of the MNP-BV hybrids.

To examine the effect of nanomagnets on BV-induced transgene expression in vitro, BV-LUC and BV-eGFP, containing luciferase and eGFP plasmids respectively, were constructed (FIG. 4a). BV-eGFP was mixed with MNPs, and the mixture was incubated with Hepa 1-6 cells under a magnetic field for 30 minutes. We found that under the applied magnetic field, the BV-MNP complex induced higher eGFP expression compared with BV alone (FIG. 4b). When BV-eGFP was mixed with MNPs labeled with a fluorophore, DiI (a fluorescent lipophilic cationic indocarbocyanine dye, ex/em=549/565 nm), MNPs could be observed in perinuclear vesicles in the cells that had a strong eGFP expression, indicating that MNPs enhanced BV uptake, and without interfering its endosomal escape (FIG. 4c). The BV transduction efficiency was determined by quantifying luciferase activity in the cells incubated with BV-LUC (FIG. 2d).

We found that MNPs or the magnetic field alone did not affect the transgene expression. Having MNPs mixed with BVs and applying magnetic field could increase the BV transduction by 2.4 fold compared with that by BV alone. No significant cell death was found following BV treatment, even at an MOI of 500, nor for the cells incubated with MNP-BV at different concentrations.

The results shown in FIG. 4 were obtained with an MNP to BV ratio of ~10[4]:1 in the MNP-BV mixture, so the vast majority of MNPs were not attached to BV. Using MNPs without the TAT peptide conjugation, we also found that nanomagnets alone could enhance the cellular uptake of BV as well as BV-LUC induced transgene expression (data not shown). The transduction efficiency of BV increases with the ratio between MNP and BV, the strength of the magnetic field and the incubation time (see FIG. 8).

It has been shown that cellular uptake of BV is mediated by actin filaments in the cells[25]. We consistently found that Hepa 1-6 cells treated with cytochalasin D, an actin depolymerization agent, showed disrupted actin filament structure and reduced BV uptake compared to control cells (not shown). However, subsequent use of MNPs together with the applied magnetic field could partially restore actin filament formation and BV uptake. These results suggest that the increase in the cellular uptake of MNP-BV complexes may be due to magnetic force-induced mechanotransduction that involves actin filaments[19, 34]. This result is quite surprising, as one might have predicted that the magnetic field effect was the result of local increases in the concentration of BV. However, if that were true, then increasing the concentration of BV should improve efficacy and it did not (data not shown).

Figure 5A:
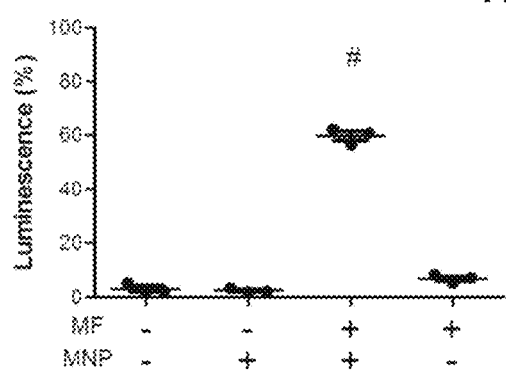
FIG. 5(a)-(b). Nanomagnets help BV overcome serum inactivation in vitro. (a) In vitro activation of transgene expression against adult mouse serum (AMS). Hepa 1-6 cells were incubated with BV or MNP-BV for 30 minutes in a culture medium contained 50% AMS. With BV alone (−/−), AMS completely inhibited BV transgene expression. Either the magnetic field alone (+/−) or MNPs alone (−/+) could not prevent BV inactivation. In contrast, MNP-BV under magnetic field (+/+) showed strong luciferase activity, indicating that both MNPs and the magnetic field are required to protect BV from serum deactivation. The luciferase activity was normalized with that from cells incubated with BV alone for 4 hours without AMS. (b) Nanomagnet induced BV activation is location-dependent. The cells cultured in a chamber slide were incubated with MNP-BV-eGFP in the culture medium containing 50% of AMS for 30 minutes, while the left half of the chamber was placed on a block magnet. Most eGFP positive cells localized in the area on top of the magnet. Data represent mean±SEM; n=3 per group. This in vitro experiment confirms our hypothesis that a strong magnetic field can protect BV-MNPs from inactivation by the complement system, allowing the expression of genes in the BV.

To determine if MNPs can protect BVs from serum inactivation similar to that of polymer coating or ligand displaying[22, 24, 25], we performed BV transduction in a culture medium containing 50% of adult mouse serum (AMS), which contains the complement system to inactivate BV. When the cells were incubated with BV alone, BV transduction was abolished by AMS as indicated by the negligible luciferase expression in the cells (FIG. 5a). Neither MNPs nor the applied magnetic field alone could rescue BV-LUC transgene expression. In contrast, in the presence of the applied magnetic field, BV-LUC associated with MNPs gave a high level of luciferase expression in Hepa 1-6 cells. We found that AMS had essentially no effect when MNP-BV-LUC was used together with an applied magnetic field, however, the transgene expression was greatly suppressed by AMS without MNP or magnetic field alone (FIGS. 4d and 5a). These results indicate that MNPs coupled with the magnetic field induce a rapid cellular uptake of BV, suggesting a drastically increased kinetic process for BV transduction that outpaced AMS-induced BV inactivation.

Figure 5B:
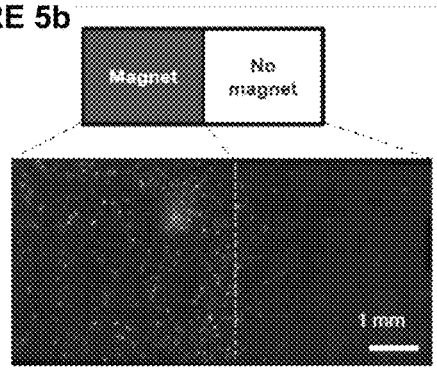

We also investigated if the serum inactivation and magnetic activation could be combined to provide spatial control of BV transduction. Cells in a chamber slide were incubated with MNP-BV-eGFP in the presence of AMS; only half of the chamber was placed on a block magnet. We found that after 12 hours post transduction, most eGFP-positive cells were in the area above the magnet (FIG. 5b).

As further proof, an artificial vein was created by growing a layer of endothelial cells in a silicone tubing. The MNP-BV-eGFP vector in culture medium containing AMS was infused into the tubing at a flow rate of 7 mm/s. A section of the tubing was placed along a block magnet during the infusion. After overnight incubation, we found that only the cells in the tubing next to the magnet showed eGFP fluorescence (data not shown), further demonstrating the ability to provide accurate spatial control of BV transduction.

Figure 2:
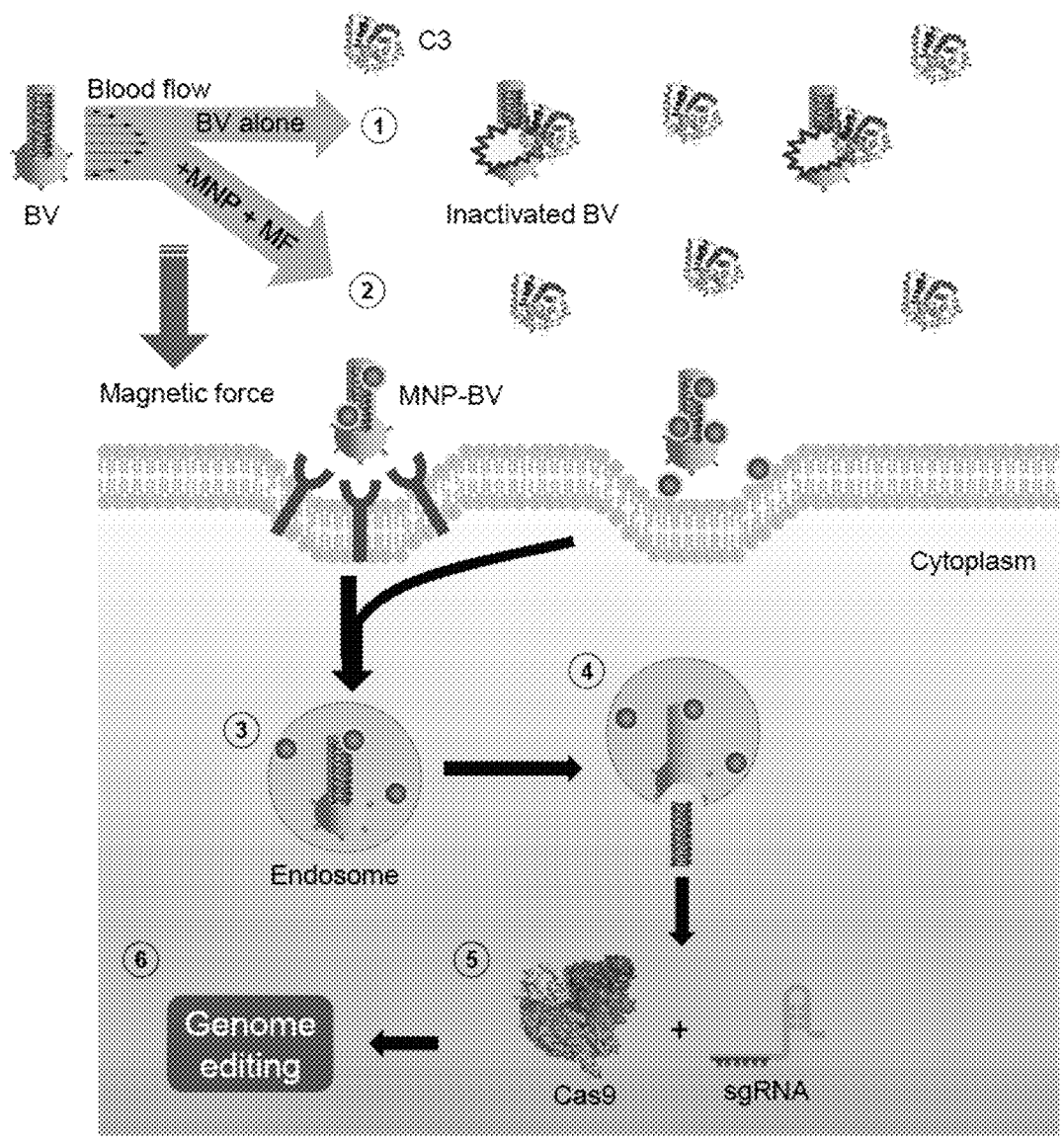
FIG. 2. BV inactivation by complement, and protective effective of magnetic nanoparticles. BV administered systemically will distribute throughout the body by blood circulation. However, complementary factor, C3, binds to circulating BV and initiates viral inactivation (1). With an applied magnetic field, MNP-BV is pulled toward the cell surface and rapidly internalized by the cells through endocytosis (2), thus avoiding the C3-mediated inactivation pathway. Once internalized, MNP-BV enters endosomes (3) and releases its genomic content into the cytoplasm upon endosomal escape (4). The large BV genome enables encoding each of the CAS9 nuclease and multiple guide RNAs and optionally donor templates for genome editing in transduced cells, (5-6). Site-specific genome editing can thus be achieved by overcoming C3-mediated viral inactivation, locally with MNP-BV and an applied magnetic field.

It was been well established that BV administrated intravenously can circulate throughout the body, where the complementary factor C3 in the blood will bind to circulating BV and initiate molecular events that lead to BV inactivation (FIG. 2, (1))[26]. In contrast, a magnetic field applied to target cells can drive MNP-BV toward cell surface and enhance its cellular uptake with faster kinetics, which overcomes BV inactivation by the complementary factor C3 (FIG. 2, (2)).

Once inside the cell, MNP-BV can escape from endosomes and releases its genomic content into the cytoplasm (FIG. 2, (3-4)). For in vivo genome editing, the released pDNA will express encoded gRNA and CAS9 in transduced cells (FIG. 2, (5-6)). Therefore, magnetic activation of BV will enable selective in vivo genome editing in just those tissues exposed to the applied magnetic field.

We tested this nanomagnet-based approach for localized gene editing in live mouse liver, which can be readily targeted with a block magnet applied externally. MNP-BV carrying the plasmid encoding luciferase (FIG. 6a) was administrated systemically through tail vein injection, and the mouse was positioned on top of a block magnet for 1 hour belly side down (FIG. 6b). The transgene expression was evaluated by examining the luciferase activity with live animal imaging.

Figure 6C:
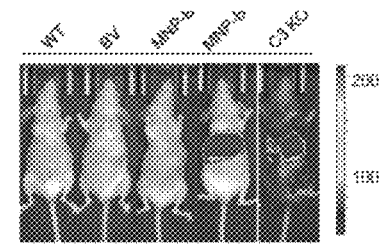
Figure 6D:
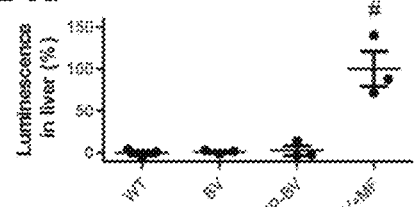

Consistent with the results from our in vitro studies, the mice treated with MNP-BV-LUC and subjected to an applied magnet field showed strong luminescence in the liver, whereas there was no luminescence in the mice treated with BV-LUC alone, or with MNP-BV-LUC but without applying a magnetic field (FIG. 6c-d).

Figure 6E:
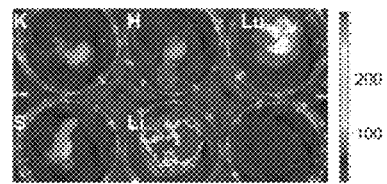
Figure 6G:
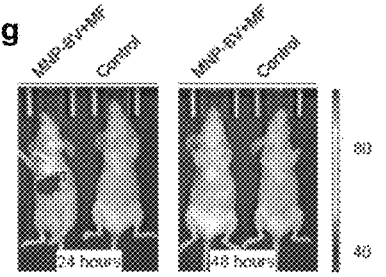
Figure 6F:
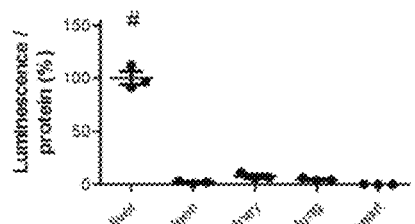
Figure 6H:
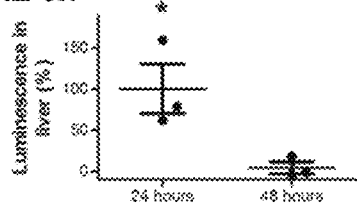

Ex vivo examination confirmed that the high luciferase expression was only in the liver tissue exposed to the magnetic field; other vital organs including heart, lung, spleen and kidney did not show luminescence signal (FIG. 6e-f). The level of luciferase expression in the liver also increased with the strength of the magnetic field (not shown). Importantly, the luciferase expression in mouse liver lasted less than 48 hours, and the MNP-BV-LUC did not induce significant acute liver damage (not shown). These results confirm that the nanomagnets induced transgene expression in vivo can be switched on remotely and locally, and the expression is transient, resulting in good spatiotemporal control. Further, the components of the method do not appear to be toxic.

To further demonstrate the spatiotemporal control of in vivo genome editing, we integrated the cassettes encoding eGFP, the *Streptococcus pyogenes* (Spy) CAS9, and gRNA targeting mouse VEGFR2 gene into one plasmid for BV packaging, thanks to its large DNA loading capacity (>38 kb) (FIG. 7a). The fluorescence from eGFP was used to determine the transduction efficiency and isolate transduced mouse cells. When delivered as plasmid and using the BV-CRISPR vector respectively into mouse Hepa 1-6 cells, the CRISPR/CAS9 system had cutting efficiencies of 9-30% of the mouse VEGFR2 gene (not shown). When Hepa 1-6 cells were incubated with the MNP-BV vector carrying CRISPR/CAS9 (MNP-BV-CRISPR) in the medium containing 50% AMS, both the eGFP expression and the CRISPR/CAS9 induced gene modification rate increased with the strength of the applied magnetic field (FIG. 7b). Without applying a magnetic field to overcome BV inactivation by AMS, there was no eGFP expression or site-specific VEGFR2 gene modification in Hepa 1-6 cells (FIG. 7b).

For in vivo genome editing, mice were injected with MNP-BV-CRISPR and subjected to a magnetic field targeting mouse liver similar to that shown in FIG. 6b. Following the workflow illustrated in FIG. 7c, after 24 hours post MNP-BV-CRISPR delivery, the eGFP positive cells were harvested from mouse liver and T7E1 assays performed to quantify the gene modification rate.

We found that the nanomagnets induced site-specific gene modification in transduced mouse liver cells with a ~50% indel rate (FIG. 7d), which is higher than that in mouse liver cells treated in vitro with MNP-BV-CRISPR as a positive control. A representative pattern of the indels at the VEGFR2 target locus is shown in FIG. 7e. Our next-generation sequencing analysis suggested that ~86% of mutations (3N+1, 3N+2) may lead to a frameshift. In a parallel experiment, mouse organs beyond the range of the magnetic field, including heart, lung, spleen, and kidney, were harvested 4 days post MNP-BV-CRISPR delivery and the genomic DNA was extracted for sequence analysis. No site-specific gene modification was detected in these off-target organs.

Figure 8A:
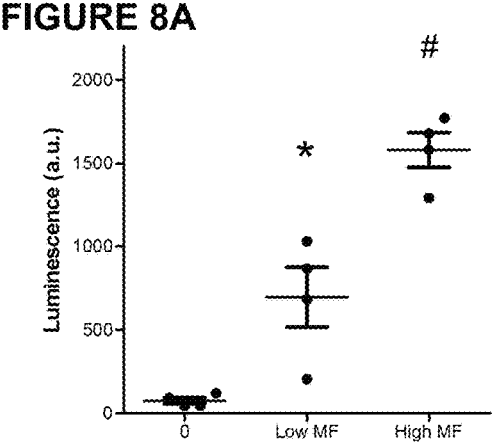
FIG. 8A-B. Factors regulating BV-mediated transgene delivery.
Figure 8B:
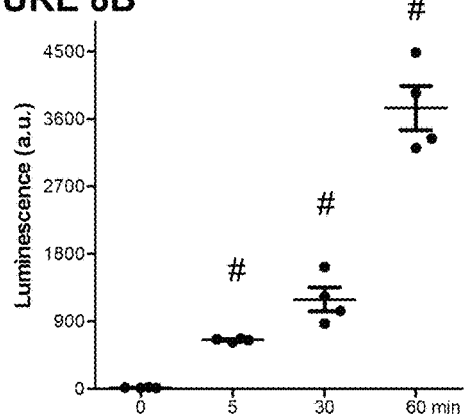
Figure 8C:
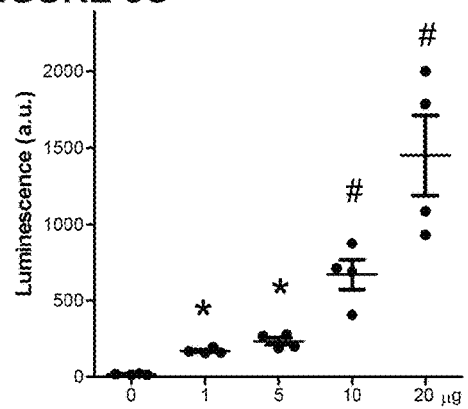

We also evaluated some of the factors affecting efficiency of the system. The transduction efficiency of MNP-BV increases with the magnetic field strength (FIG. 8). The transduction efficiency also increases as the length of magnetic treatment increases from 5 to 60 minutes, or when the ratio between MNP and BV increases from 500:1 to 10,000:1.

Taken together, the results conclusively demonstrate that the MNP-BV system can deliver CRISPR/CAS9 in vivo, and the nuclease activity in target tissues/organ can be induced by an external magnetic field in a site-specific manner. The MNP-BV based delivery system takes advantage of the ability of nanomagnets to overcome BV serum-inactivation locally, thus enabling spatiotemporal control of in vivo genome editing. Owing to the large DNA loading capacity of BV, this system has the potential to facilitate multiplexed genome editing in vivo.

The following references are incorporated by reference herein in its entirety for all purposes:

1. Sander, J. D. & Joung, J. K. CRISPR-Cas systems for editing, regulating and targeting genomes. *Nat Biotechnol* 32, 347-355 (2014).
2. Cong, L. et al. Multiplex Genome Engineering Using CRISPR/Cas Systems. *Science* 339, 819-823 (2013).
3. Yin, H. et al. Genome editing with CAS9 in adult mice corrects a disease mutation and phenotype. *Nat Biotechnol* 32, 551-553 (2014).
4. Swiech, L. et al. In vivo interrogation of gene function in the mammalian brain using CRISPR-CAS9. *Nat Biotechnol* 33, 102-106 (2015).
5. Cox, D. B., Platt, R. J. & Zhang, F. Therapeutic genome editing: prospects and challenges. *Nat Med* 21, 121-131 (2015).

6. Liao, H. K. et al. Use of the CRISPR/CAS9 system as an intracellular defense against HIV-1 infection in human cells. *Nat Commun* 6, 6413 (2015).
7. Lin, Y. N. et al. CRISPR/CAS9 systems have off-target activity with insertions or deletions between target DNA and guide RNA sequences. *Nucleic Acids Research* 42, 7473-7485 (2014).
8. Cradick, T. J., Fine, E. J., Antico, C. J. & Bao, G. CRISPR/CAS9 systems targeting beta-globin and CCR5 genes have substantial off-target activity. *Nucleic Acids Research* 41, 9584-9592 (2013).
9. Fu, Y. et al. High-frequency off-target mutagenesis induced by CRISPR-Cas nucleases in human cells. *Nat Biotechnol* 31, 822-826 (2013).
10. Hsu, P. D. et al. DNA targeting specificity of RNA-guided CAS9 nucleases. *Nat Biotechnol* 31, 827-832 (2013).
11. Lee, C. M., Cradick, T. J., Fine, E. J. & Bao, G. Nuclease Target Site Selection for Maximizing On-target Activity and Minimizing Off-target Effects in Genome Editing. *Mol Ther* 24, 475-487 (2016).
12. Dow, L. E. et al. Inducible in vivo genome editing with CRISPR-CAS9. *Nat Biotechnol* 33, 390-394 (2015).
13. Nihongaki, Y., Kawano, F., Nakajima, T. & Sato, M. Photoactivatable CRISPR-CAS9 for optogenetic genome editing. *Nat Biotechnol* 33, 755-760 (2015).
14. Pansare, V., Hejazi, S., Faenza, W. & Prud'homme, R. K. Review of Long-Wavelength Optical and NIR Imaging Materials: Contrast Agents, Fluorophores and Multifunctional Nano Carriers. *Chem Mater* 24, 812-827 (2012).
15. Zincarelli, C., Soltys, S., Rengo, G. & Rabinowitz, J. E. Analysis of AAV Serotypes 1-9 Mediated Gene Expression and Tropism in Mice After Systemic Injection. *Molecular Therapy* 16, 1073-1080 (2008).
16. Yin, H. et al. Therapeutic genome editing by combined viral and non-viral delivery of CRISPR system components in vivo. *Nat Biotechnol* 34, 328-333 (2016).
17. Wang, Y. et al. Systemic dissemination of viral vectors during intratumoral injection. *Mol Cancer Ther* 2, 1233-1242 (2003).
18. Stanley, S. A., Sauer, J., Kane, R. S., Dordick, J. S. & Friedman, J. M. Remote regulation of glucose homeostasis in mice using genetically encoded nanoparticles. *Nat Med* 21, 92-98 (2015).
19. Mannix, R. J. et al. Nanomagnetic actuation of receptor-mediated signal transduction. *Nat Nanotechnol* 3, 36-40 (2008).
20. Wheeler, M. A. et al. Genetically targeted magnetic control of the nervous system. *Nat Neurosci* 19, 756-761 (2016).
21. Sammet, S. Magnetic resonance safety. *Abdom Radiol* 41, 444-451 (2016).
22. Airenne, K. J. et al. Baculovirus: an insect-derived vector for diverse gene transfer applications. *Mol Ther* 21, 739-749 (2013).
23. Mansouri, M. et al. Highly efficient baculovirus-mediated multigene delivery in primary cells. *Nat Commun* 7, 11529 (2016).
24. Chen, C. Y., Lin, C. Y., Chen, G. Y. & Hu, Y. C. Baculovirus as a gene delivery vector: recent understandings of molecular alterations in transduced cells and latest applications. *Biotechnol Adv* 29, 618-631 (2011).
25. Kost, T. A., Condreay, J. P. & Jarvis, D. L. Baculovirus as versatile vectors for protein expression in insect and mammalian cells. *Nat Biotechnol* 23, 567-575 (2005).
26. Hofmann, C. & Strauss, M. Baculovirus-mediated gene transfer in the presence of human serum or blood facilitated by inhibition of the complement system. *Gene Ther* 5, 531-536 (1998).
27. Kaikkonen, M. U., Maatta, A. I., Yla-Herttuala, S. & Airenne, K. J. Screening of complement inhibitors: shielded baculoviruses increase the safety and efficacy of gene delivery. *Mol Ther* 18, 987-992 (2010).
28. Raty, J. K. et al. Enhanced gene delivery by avidin-displaying baculovirus. *Mol Ther* 9, 282-291 (2004).
29. Sun, S. et al. Monodisperse MFe2O4 (M=Fe, Co, Mn) nanoparticles. *J Am Chem Soc* 126, 273-279 (2004).
30. Tong, S., Hou, S., Ren, B., Zheng, Z. & Bao, G. Self-assembly of phospholipid-PEG coating on nanoparticles through dual solvent exchange. *Nano Lett* 11, 3720-3726 (2011).
31. Torchilin, V. P. Tat peptide-mediated intracellular delivery of pharmaceutical nanocarriers. *Adv Drug Deliv Rev* 60, 548-558 (2008).
32. Boyce, F. M. & Bucher, N. L. R. Baculovirus-mediated gene transfer into mammalian cells. *P Natl Acad Sci USA* 93, 2348-2352 (1996).
33. Matilainen, H. et al. Baculovirus entry into human hepatoma cells. *J Virol* 79, 15452-15459 (2005).
34. Romet-Lemonne, G. & Jegou, A. Mechanotransduction down to individual actin filaments. *European journal of cell biology* 92, 333-338 (2013).
35. Danquah, J. O., Botchway, S., Jeshtadi, A. & King, L. A. Direct interaction of baculovirus capsid proteins VP39 and EXON0 with kinesin-1 in insect cells determined by fluorescence resonance energy transfer-fluorescence lifetime imaging microscopy. *J Virol* 86, 844-853 (2012).

What is claimed is:

1. A method of targeted in vivo gene editing, said method comprising:
   a) packaging an expression vector encoding a CAS9 or dCAS9 protein, single or multiple guide RNAs and an optional donor template into a baculovirus vector (BV), wherein said guide RNA and said optional donor template have homology to one or more gene(s) that is to be edited;
   b) attaching a plurality of magnetic nanoparticles (MNP) of <200 nm average size to said BV to make MNP-BV, wherein said MNP:BV ratio is at least 500:1;
   c) introducing said MNP-BV to a patient comprising said gene(s) to be edited, wherein the MNP-BV contacts the patient's blood;
   d) applying a magnetic field to a targeted tissue within 30 minutes of said introducing step c, without applying said magnetic field to non-targeted tissue, so that the MNP-BV are only taken up and expressed in cells in said targeted tissue and MNP-BV is inactivated by a complement system outside of the magnetic field; and
   e) thereby editing said gene(s) only in said targeted tissue in said patient.

2. The method of claim 1, wherein said magnetic field is at least 0.1 Tesla.

3. The method of claim 1, wherein said gradient of the magnetic field is at least 0.1 Tesla/m.

4. The method of claim 1, wherein said magnetic field is applied within 10 minutes of said introducing step c.

5. The method of claim 4, wherein said magnetic field is applied for at least 30 minutes.

6. The method of claim 1, wherein said magnetic field is applied for at least 60 minutes.

7. The method of claim 1, wherein said MNP:BV ratio is at least $10^4$:1.

8. The method of claim 2, wherein said MNP:BV ratio is at least $10^4$:1.

9. The method of claim 1, wherein said guide RNA is a synthetic guide RNA comprising a gRNA and a trRNA.

10. A method of targeted in vivo gene editing, said method comprising:

a) packaging an expression vector encoding a CRISPR nuclease, single or multiple guide RNAs and an optional donor template into a baculovirus vector (BV), wherein said guide RNA and said donor template have homology to one or more gene(s) that is to be edited in a targeted tissue;

b) attaching a plurality of magnetic nanoparticles (MNP) to said BV to make MNP-BV, wherein a ratio of MNP to BV is at least 500:1 and the MNPs have an average size smaller than 200 nm;

c) systemically introducing said MNP-BV to a patient having said gene to be edited;

d) applying a magnetic field of at least 0.1 Tesla and 0.1 Tesla/m to said targeted tissue within 10 minutes of said introducing step c, without applying said magnetic field to non-targeted tissue, so that the MNP-BV are only taken up and transiently expressed in cells in said targeted tissue and MNP-BV is inactivated by a complement system in said patient outside of the magnetic field; and e) thereby editing said gene only in said targeted tissue in said patient.

11. The method of claim 10, wherein said MNP are made with iron oxide nanoparticles.

12. The method of claim 10, wherein said MNP are made with iron(III) oxide nanoparticles and said nanoparticles are coated with one or more biocompatible polymers.

13. The method of claim 10, wherein said MNP are made with magnetite crystals of 10-50 nm and said crystals inside a biocompatible phospholipid micelle.

14. The method of claim 12, wherein said nanoparticles are conjugated with ligands that bind to the BV surface.

15. The method of claim 10, wherein said MNP:BV ratio is at least $10^4$:1.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: CRISPR primer

<400> SEQUENCE: 1
cccccattcg ctagtgtgta                                              20

<210> SEQ ID NO 2
<211> LENGTH: 20

-continued

```
<212> TYPE: DNA
<213> ORGANISM: Artificial Sequence
<220> FEATURE:
<223> OTHER INFORMATION: CRISPR primer

<400> SEQUENCE: 2
agcacggagt gattgatgcc                                              20

<210> SEQ ID NO 3
<211> LENGTH: 21
<212> TYPE: DNA
<213> ORGANISM: Artificial Sequence
<220> FEATURE:
<223> OTHER INFORMATION: CRISPR primer

<400> SEQUENCE: 3
tgaaagaaca cccaagggag g                                            21

<210> SEQ ID NO 4
<211> LENGTH: 20
<212> TYPE: DNA
<213> ORGANISM: Artificial Sequence
<220> FEATURE:
<223> OTHER INFORMATION: CRISPR primer

<400> SEQUENCE: 4
gggacggaga aggagtctgt                                              20

<210> SEQ ID NO 5
<211> LENGTH: 43
<212> TYPE: DNA
<213> ORGANISM: mouse

<400> SEQUENCE: 5
gctgctagct gtcgctctgt ggttctgcgt ggagacccga gcc                    43

<210> SEQ ID NO 6
<211> LENGTH: 33
<212> TYPE: DNA
<213> ORGANISM: mouse

<400> SEQUENCE: 6
gctgctagct gtcgctctgt ggagacccga gcc                               33

<210> SEQ ID NO 7
<211> LENGTH: 36
<212> TYPE: DNA
<213> ORGANISM: mouse

<400> SEQUENCE: 7
gctgctagct gtcgctctgt ggtggggacc cgagcc                            36

<210> SEQ ID NO 8
<211> LENGTH: 38
<212> TYPE: DNA
<213> ORGANISM: mouse

<400> SEQUENCE: 8
gctgctagct gtcgctctgt ggcgtggaga cccgagcc                          38

<210> SEQ ID NO 9
<211> LENGTH: 40
<212> TYPE: DNA
<213> ORGANISM: mouse
```

```
<400> SEQUENCE: 9
gctgctagct gtcgctctgt ggttcttgga gacccgagcc                              40

<210> SEQ ID NO 10
<211> LENGTH: 40
<212> TYPE: DNA
<213> ORGANISM: mouse

<400> SEQUENCE: 10
gctgctagct gtcgctctgt ggtgcgtgga gacccgagcc                              40

<210> SEQ ID NO 11
<211> LENGTH: 41
<212> TYPE: DNA
<213> ORGANISM: mouse

<400> SEQUENCE: 11
gctgctagct gtcgctctgt ggttccgtgg agacccgagc c                            41

<210> SEQ ID NO 12
<211> LENGTH: 42
<212> TYPE: DNA
<213> ORGANISM: mouse

<400> SEQUENCE: 12
gctgctagct gtcgctctgt ggttcgcgtg gagacccgag cc                           42

<210> SEQ ID NO 13
<211> LENGTH: 44
<212> TYPE: DNA
<213> ORGANISM: mouse

<400> SEQUENCE: 13
gctgctagct gtcgctctgt ggttcatgcg tggagacccg agcc                         44

<210> SEQ ID NO 14
<211> LENGTH: 45
<212> TYPE: DNA
<213> ORGANISM: mouse

<400> SEQUENCE: 14
gctgctagct gtcgctctgt ggttcaatgc gtggagaccc gagcc                        45
```